(12) United States Patent
Margaria

(10) Patent No.: US 12,059,252 B2
(45) Date of Patent: Aug. 13, 2024

(54) MONITORING BLOOD OXYGEN SATURATION LEVELS OF A PATIENT INTERFACE

(71) Applicant: KONINKLIJKE PHILIPS N.V., Eindhoven (NL)

(72) Inventor: Elizabeth Powell Margaria, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 772 days.

(21) Appl. No.: 17/032,431

(22) Filed: Sep. 25, 2020

(65) Prior Publication Data

US 2021/0093236 A1    Apr. 1, 2021

Related U.S. Application Data

(60) Provisional application No. 62/906,777, filed on Sep. 27, 2019.

(51) Int. Cl.
*A61M 16/06* (2006.01)
*A61B 5/00* (2006.01)
*A61B 5/1455* (2006.01)

(52) U.S. Cl.
CPC ........ *A61B 5/14551* (2013.01); *A61B 5/0002* (2013.01); *A61B 5/6803* (2013.01); *A61M 16/0666* (2013.01); *A61M 2230/20* (2013.01)

(58) Field of Classification Search
CPC ........ A61B 2562/182; A61B 2562/247; A61B 5/0088; A61B 5/0878; A61B 5/14552; A61B 5/1459; A61B 5/282; A61B 5/296; A61B 5/369; A61B 5/412; A61B 5/6803; A61B 5/682; A61B 5/6826; A61B 5/6838; A61B 5/6855; A61M 16/0066;
(Continued)

(56) References Cited

U.S. PATENT DOCUMENTS

| 5,205,281 | A | 4/1993 | Buchanan |
| 5,282,464 | A | 2/1994 | Brain |

(Continued)

FOREIGN PATENT DOCUMENTS

WO    2005065540 A1    7/2005

OTHER PUBLICATIONS

International Search Report for PCT/EP2020/075322 dated Sep. 10, 2020.
(Continued)

*Primary Examiner* — Annette Dixon
(74) *Attorney, Agent, or Firm* — Michael W. Haas

(57) ABSTRACT

A tubing assembly for use in providing a flow of positive pressure breathing gas to a patient. The tubing assembly includes a manifold portion structured to receive the flow of positive pressure breathing gas, a number of tubular portions which each extend from the manifold portion to a distal end which is structured to be coupled to a patient interface for use in delivering the flow of positive pressure breathing gas to the patient, and a reflectance pulse oximetry sensor positioned in or on one of the number of tubular portions. The sensor is structured to be disposed adjacent the patient when the tubing assembly is disposed on the patient for determining blood oxygen saturation levels of the patient.

13 Claims, 4 Drawing Sheets

(58) Field of Classification Search
CPC ............ A61M 16/021; A61M 16/0488; A61M 16/049; A61M 16/0493; A61M 16/0495; A61M 16/06; A61M 16/0605; A61M 16/0611; A61M 16/0616; A61M 16/0622; A61M 16/0633; A61M 16/0666; A61M 16/0672; A61M 16/0683; A61M 16/0694; A61M 16/0816; A61M 16/0825; A61M 16/0833; A61M 16/0858; A61M 16/0875; A61M 16/16; A61M 2016/0027; A61M 2202/0085; A61M 2202/0225; A61M 2205/02; A61M 2205/0238; A61M 2205/3313; A61M 2205/3331; A61M 2205/3569; A61M 2205/42; A61M 2207/00; A61M 2210/0618; A61M 2230/04; A61M 2230/08; A61M 2230/10; A61M 2230/205; A61M 2230/30; A61M 2230/50; A61M 2230/60; A61M 2230/62; A61M 2230/63

See application file for complete search history.

(56) References Cited

U.S. PATENT DOCUMENTS

| | | | |
|---|---|---|---|
| 5,538,000 A * | 7/1996 | Rudolph | A61M 16/0672 128/207.18 |
| 6,199,550 B1 | 3/2001 | Wiesmann et al. | |
| 6,256,524 B1 * | 7/2001 | Walker | A61B 5/1459 128/200.26 |
| 8,452,367 B2 | 5/2013 | Bebout et al. | |
| 9,399,106 B2 | 7/2016 | Borody | |
| 9,668,661 B2 | 6/2017 | Melker et al. | |
| 10,206,571 B2 | 2/2019 | Chen | |
| 11,590,310 B2 * | 2/2023 | Barlow | A61M 16/0875 |
| 2002/0038082 A1 * | 3/2002 | Chin | A61B 5/6826 600/323 |
| 2004/0163648 A1 * | 8/2004 | Burton | A61M 16/0694 128/204.21 |
| 2008/0060649 A1 * | 3/2008 | Veliss | A61M 16/06 128/207.18 |
| 2013/0125891 A1 | 5/2013 | Eddy | |
| 2014/0076317 A1 | 3/2014 | Diacopoulos | |
| 2017/0333658 A1 * | 11/2017 | Haibach | A61M 16/0875 |
| 2018/0049654 A1 | 2/2018 | Gravenstein et al. | |

OTHER PUBLICATIONS

Owens, R.L. et al. "Sleep-Disordered Breathing and COPD: The Overlap Syndrome". Respir Care. Oct. 2010; 55(10): 1333-1346.
Shawson, S.R. et al., "Current evidence on prevalence and clinical outcomes of co-morbid obstructive sleep apnea and chronic obstructive pulmonary disease: A systematic review." Sleep Medicine Reviews. Feb. 2017; 32: 58-68.
McNicholas, W.T. et al., "Nocturnal deaths among patients with chronic bronchitis and emphysema". British Medical Journal. Oct. 1984 ; 289(6).

* cited by examiner

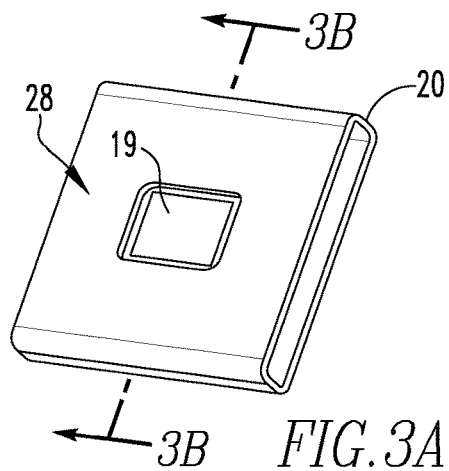
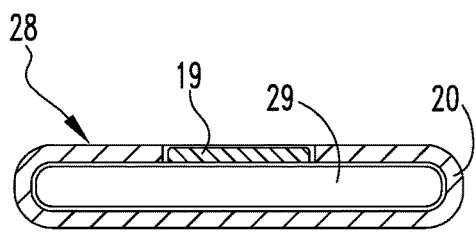
FIG.3A
FIG.3B
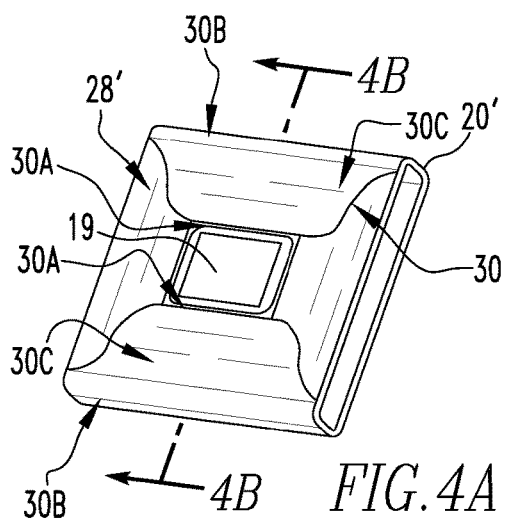
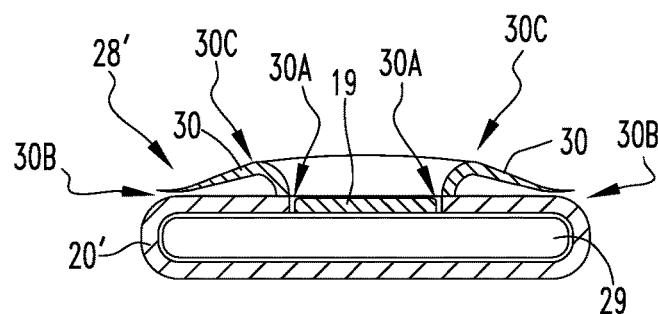
FIG.4A
FIG.4B
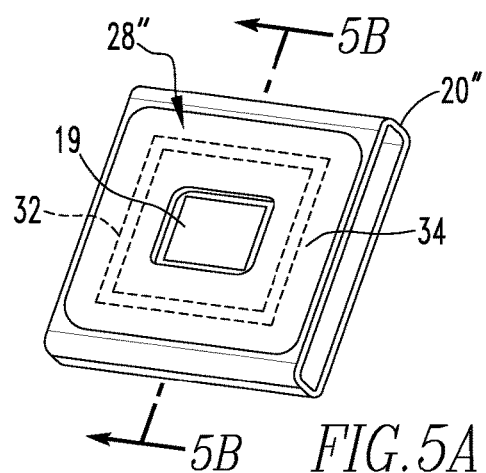
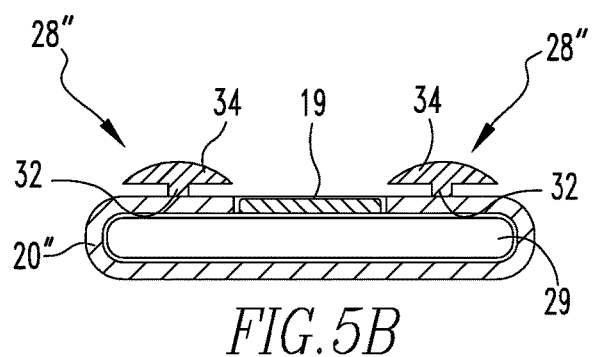
FIG.5A
FIG.5B

MONITORING BLOOD OXYGEN SATURATION LEVELS OF A PATIENT INTERFACE

CROSS-REFERENCE TO RELATED APPLICATIONS

This patent application claims the priority benefit under 35 U.S.C. § 119(e) of U.S. Provisional Application No. 62/906,777 filed on Sep. 27, 2019, the contents of which are herein incorporated by reference.

BACKGROUND OF THE INVENTION

1. Field of the Invention

The present invention pertains to methods and apparatus for integrating pulse oximetry into patient interface devices that are structured to deliver a flow of breathing gas to a user.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) to treat a medical disorder, such as chronic obstructive pulmonary disease (COPD) or sleep apnea syndrome, in particular, obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle.

COPD affects approximately 20 million people in the United States alone. A large percentage of these patients also have OSA, although the exact percentage is unknown. COPD and OSA tend to be treated separately, but when they occur together, there is a higher risk of additional comorbidities and nocturnal oxygen desaturations tend to be worse. This additive effect has implications for the quality of life, exacerbations, morbidity, and mortality of these patients, thus making it vitally important to pursue technologies which could help these patients.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from a pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask component of the device in a tight enough seal against the patient's face without discomfort.

A number of known patient interface devices provide airflow to the patient through the headgear via one or more delivery conduits that wrap around portions of the patient's head as part of the headgear. That is, the headgear includes a tubing assembly with a manifold. The manifold is coupled to, and in fluid communication with, a delivery conduit. The delivery conduit is further coupled to, and in fluid communication with, the pressure/flow generating device.

PAP therapies are typically provided to the patient at night while the patient is sleeping. One study suggests that patients with hypoxemia and hypercapnia have a higher incidence of nocturnal deaths. Monitoring nocturnal desaturations could help monitor a patient's condition, and improve patient outcomes by indicating whether or not current therapies are working effectively for the patient. For example, if a patient's oxygen desaturations worsen over time, the patient may need to be put on oxygen if they are not already. Alternatively, the delivery of therapy may need to be adjusted, e.g. the patient may need oxygen increased or a different Bilevel PAP (BiPAP®) setting.

Current methods for monitoring nocturnal oxygen desaturations utilize pulse oximetry (SpO2) sensors, which are typically found in the form of a finger probe. People tend to find these probes obtrusive and uncomfortable, and they are likely to fall off during the night. Accordingly, there is room for improvement in apparatus and methods for monitoring blood oxygen saturation levels of a patient.

SUMMARY OF THE INVENTION

As one aspect of the invention, a tubing assembly for use in providing a flow of positive pressure breathing gas to a patient is provided. The tubing assembly comprises: a manifold portion that is structured to receive the flow of positive pressure breathing gas; a number of tubular portions which each extend from the manifold portion to a distal end which is structured to be coupled to a patient interface for use in delivering the flow of positive pressure breathing gas to the patient; and a reflectance pulse oximetry sensor positioned in or on one of the number of tubular portions, wherein the sensor is structured to be disposed adjacent the patient when the tubing assembly is disposed on the head of the patient.

The sensor may be adhered to a surface of the one of the number of tubular portions.

The sensor may be coupled to the one of the number of tubular portions via over-molding.

The soft removable covering may be coupled to the one of the number of tubular portions, and the sensor may be positioned in or on the removable covering.

The sensor may be positioned with respect to the one of the number of tubular portions such that when the tubing assembly is disposed on the head of the patient the sensor is positioned on a region of the patient's face extending between a forward boundary that extends between the patient's subnasale and labiale superius and a rearward boundary that extends between the patient's temple and helical root.

The one of the number of tubular portions may comprise a skirt portion that is disposed about the sensor, and the skirt portion may be structured to shield the sensor from ambient light when the tubing assembly is disposed on the head of the patient. The skirt portion may comprise a flexible and opaque polymer. The skirt portion may include a number of protrusions each of which, when viewed in a sectional view, has an asymmetrically curved top edge that peaks toward the center of the sectional view and tapers downward toward an edge of the sectional view, and the number of protrusions may provide additional cushioning when the tubing assembly is disposed on the head of the patient. The skirt portion may include a number of protrusions each of which, when viewed in a sectional view, has a narrow stem portion arising from a surface of the skirt portion and a bulbous top edge, and the number of protrusions may provide additional cushioning when the tubing assembly is disposed on the head of the patient.

The tubing assembly may further comprise a data communication arrangement, the data communication arrangement comprising: a flexible circuit positioned in or on the same one of the number of tubular portions in or on which the sensor is positioned, the flexible circuit extending between a first end electrically connected to the sensor and an opposite second end; and one of either: an electrical connector electrically connected to the second end, the electrical connector being structured to be electrically connected to a data processor, or a wireless transmitter electrically connected to the second end, the wireless transmitter being structured to communicate wirelessly with the data processor. The flexible circuit may be structured to be disposed adjacent the patient when the tubing assembly is disposed on the head of the patient.

As another aspect of the invention, a mask for use in providing a flow of positive pressure breathing gas to a patient is provided. The mask comprises: a tubing assembly structured to receive the flow of positive pressure breathing gas, the tubing assembly comprising: a manifold portion structured to receive the flow of positive pressure breathing gas; and a number of tubular portions which each extend from the manifold portion to a distal end; a patient interface coupled to the distal end of each tubular portion for conveying the flow of positive pressure breathing gas to an airway of the patient; and a reflectance pulse oximetry sensor positioned in or on one of the number of tubular portions, wherein the sensor is structured to be disposed adjacent the patient when the mask is disposed on the head of the patient.

The mask may further comprise a data communication arrangement, the data communication arrangement comprising: a flexible circuit positioned in or on the same one of the number of tubular portions in or on which the sensor is positioned, the flexible circuit extending between a first end electrically connected to the sensor and an opposite second end; and one of either: an electrical connector electrically connected to the second end, the electrical connector being structured to be electrically connected to a data processor, or a wireless transmitter electrically connected to the second end, the wireless transmitter being structured to communicate wirelessly with the data processor.

As yet another aspect of the invention, a method for measuring a blood oxygen saturation level of a patient is provided. The method comprises: providing the patient with a mask for use in providing a flow of positive pressure breathing gas to the patient, the mask comprising: a tubing assembly structured to receive the flow of positive pressure breathing gas, the tubing assembly comprising: a manifold portion structured to receive the flow of positive pressure breathing gas; and a number of tubular portions which each extend from the manifold portion to a distal end; a patient interface coupled to the distal end of each tubular portion for conveying the flow of positive pressure breathing gas to an airway of the patient; a reflectance pulse oximetry sensor positioned in or on one of the number of tubular portions, wherein the sensor is structured to be disposed adjacent the patient when the mask is disposed on the head of the patient; and a data communication arrangement, the data communication arrangement comprising: a flexible circuit positioned in or on the same one of the number of tubular portions in or on which the sensor is positioned, the flexible circuit extending between a first end electrically connected to the sensor and an opposite second end; and one of either: an electrical connector electrically connected to the second end, the electrical connector being structured to be electrically connected to a data processor, or a wireless transmitter electrically connected to the second end, the wireless transmitter being structured to communicate wirelessly with the data processor; and detecting data about the blood oxygen saturation level of the patient with the sensor after the mask has been disposed on the head of the patient.

The method may further comprise: providing the flow of breathing gas to the patient via the mask; and altering the flow of breathing gas provided to the patient in response to the blood oxygen saturation level detected with the sensor.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 3A is a partially schematic perspective view of a skirt arrangement about an oximetry sensor in accordance with one example embodiment of the present invention;

FIG. 3B is a sectional view of the skirt arrangement of FIG. 3A as indicated by line B-B in FIG. 3A;

FIG. 4A is a partially schematic perspective view of a another skirt arrangement about an oximetry sensor in accordance with one example embodiment of the present invention;

FIG. 4B is a sectional view of the skirt arrangement of FIG. 4A as indicated by line B-B in FIG. 4A;

FIG. 5A is a partially schematic perspective view of yet another skirt arrangement about an oximetry sensor in accordance with one example embodiment of the present invention; and FIG. 5B is a sectional view of the skirt arrangement of FIG. 5A as indicated by line B-B in FIG. 5A.

DETAILED DESCRIPTION OF EXEMPLARY EMBODIMENTS

Figure 1:
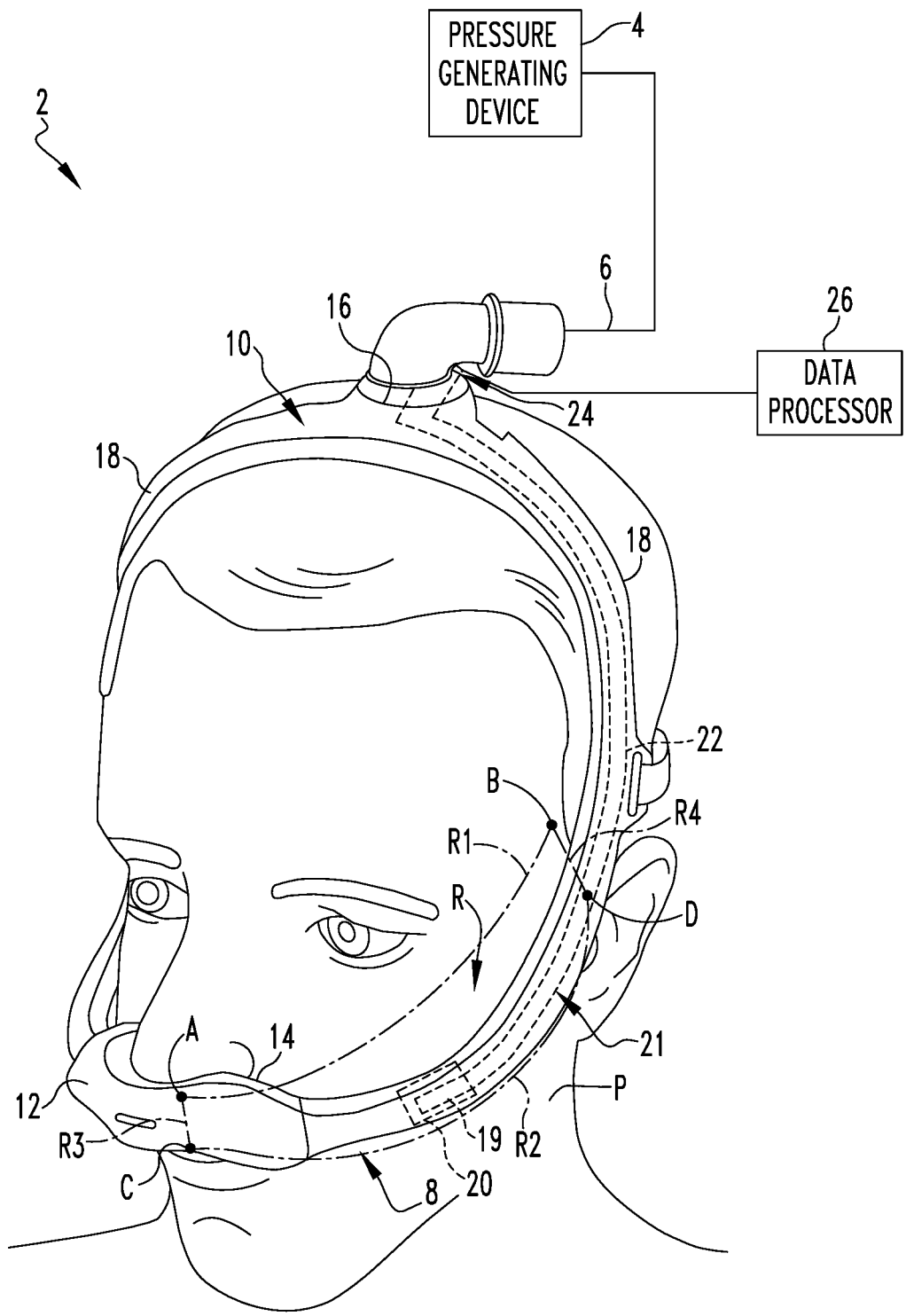
FIG. 1 is a partially schematic depiction of a respiratory interface system for use in providing a flow of positive pressure breathing gas to the airway of a patient in accordance with one example embodiment of the present invention, shown with a mask thereof disposed on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components.

As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

A respiratory interface system 2 adapted to provide a regimen of respiratory therapy to a patient P according to one exemplary embodiment of the present invention is shown in FIG. 1. Respiratory interface system 2 includes a pressure generating device 4 (shown schematically), and a delivery conduit 6 fluidly coupled to a mask 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to mask 8, and mask 8 is structured to further communicate the flow of breathing gas received from conduit 6 to an airway of patient P. Delivery conduit 6 and mask 8 are often collectively referred to as a patient circuit.

Mask 8 includes a tubing assembly 10 and a patient interface 12 fluidly coupled to tubing assembly 10. Patient interface 12 includes a patient sealing element 14 which is structured to sealingly engage about one or more of the nares and/or mouth of patient P. In one example embodiment as illustrated in FIG. 1, patient sealing element 14 is a nasal cushion made of a soft, flexible material, such as, without limitation, silicone, an appropriately soft thermoplastic elastomer, a closed-cell foam, or any other suitable material or combination of such materials. It is to be appreciated, however, that any type of patient sealing element, such as a nasal/oral mask, a nasal pillow or a full face mask, which facilitates the delivery of the flow of breathing gas to the airway of a patient, may be used as sealing element 14.

Figure 2A:
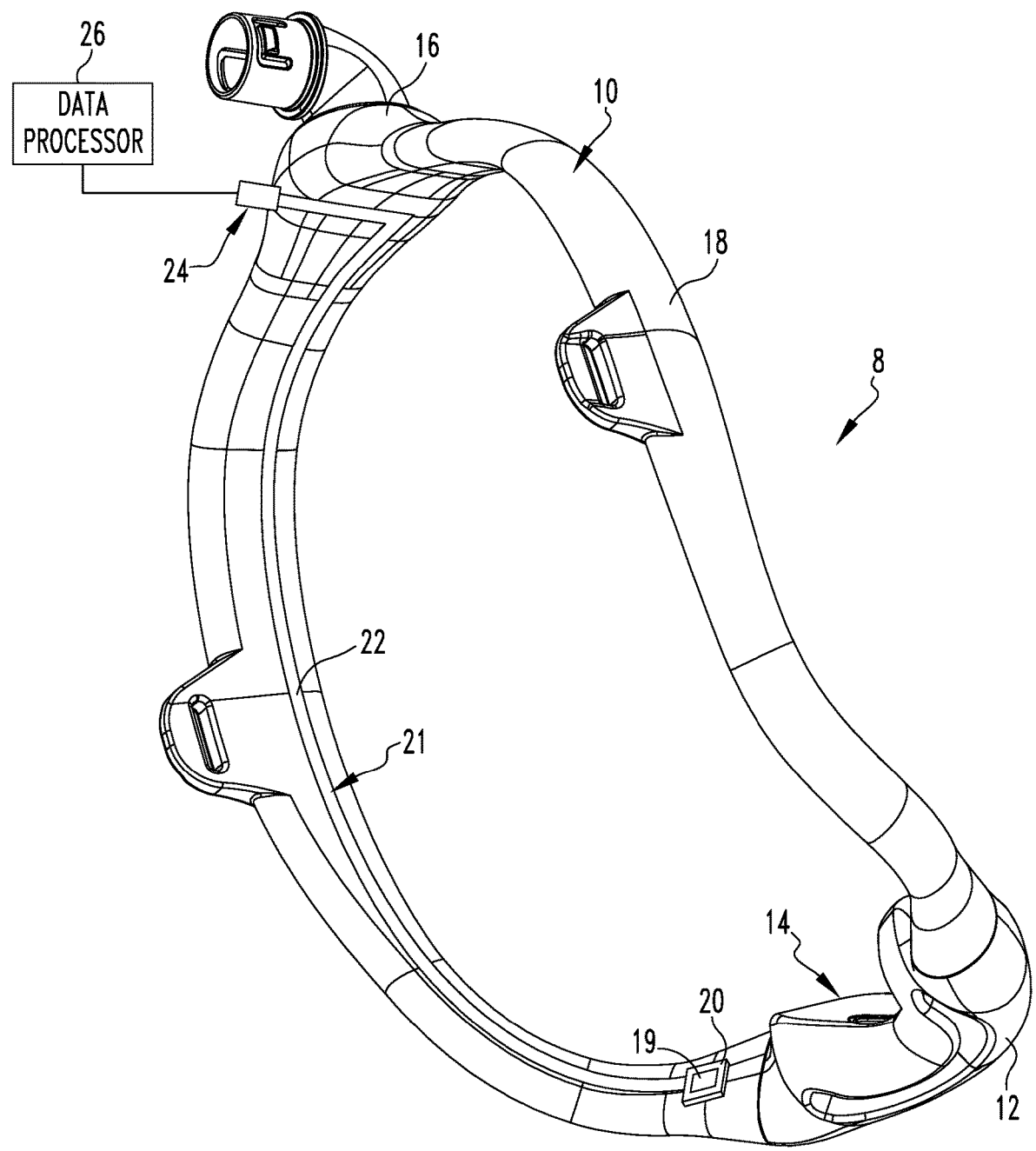
FIG. 2A is a partially schematic perspective view of the mask of the system of FIG. 1 showing a patient contacting portion thereof.

Continuing to refer to FIG. 1, as well as to FIG. 2A, tubing assembly 10 includes a manifold portion 16 structured to receive the flow of positive pressure breathing gas from delivery conduit 6, a number (two are shown in the example of FIG. 1) of tubular portions 18 which each extend from manifold portion 16 to a distal end (not numbered) which is selectively coupled to patient interface 12. Tubing assembly 10 further includes a reflectance pulse oximetry sensor 19 (shown schematically) coupled to one of tubular portions 18. Pulse oximetry sensor 19 is positioned to lie immediately adjacent to the face of patient P when tubing assembly 10 is disposed on patient P in order to monitor the blood oxygen saturation level of patient P while patient P is receiving a treatment via mask 8.

In the example shown in FIGS. 1, 2A and 2B, pulse oximetry sensor 19 is disposed (e.g., via sliding) within a pocket 20 which may either be formed integrally with one tubular portion 18 or formed separately and subsequently coupled thereto via any suitable process. Although shown being coupled to tubular portion 18 via pocket 20, it is to be appreciated that pulse oximetry sensor 19 can be directly coupled to one of tubular portions 18 via any suitable arrangement (e.g., without limitation, adhesive, over-molding) without varying from the scope of the present invention. Alternatively, pulse oximetry sensor 19 can be coupled to a soft removable covering that is then affixed, either permanently or selectively, around one of tubular portions 18. In one exemplary embodiment, pulse oximetry sensor 19 is coupled to a fabric covering provided with both a hook-portion and a loop-portion of a hook-and-loop fastener arrangement such that the fabric covering can be securely wrapped around one of tubular portions 18 and generally secured thereto via engagement of the hook and loop portions.

FIG. 1 further generally shows a region R of the face of patient P that has been found to yield acceptably accurate data about the blood oxygen saturation level of patient P when pulse oximetry sensor 19 is disposed adjacent to patient P in or near region R. Accordingly, in one exemplary embodiment of the invention, pulse oximetry sensor 19 is coupled to a section of one of tubular portions 18 that coincides with region R when tubing assembly 10 is disposed on the head of patient P. Region R is generally defined vertically by an upper curved line R1 that extends between the subnasale (shown generally by point A) and temple (shown generally by point B) of patient P, a lower curved line R2 that extends between the labiale superius (shown generally by point C) and helical root of the ear (shown generally by point D); and generally defined horizontally by a forward vertical line R3 that extends between the subnasale and labiale superius (points A and C) of patient P and a rearward generally vertical line R4 that extends between the temple and root of the ear (points B and D).

It is to be appreciated, however, that other regions of the head of patient P can yield reasonably accurate data about the blood oxygen saturation level of patient P when pulse oximetry sensor 19 is disposed adjacent to patient P in or near such regions. For example, in an alternative embodiment of the invention, pulse oximetry sensor 19 could be disposed adjacent to an ear of patient P.

Referring again to FIGS. 1 and 2A, tubing assembly 10 further includes a data communication arrangement 21 that includes a flexible circuit 22 electrically connects pulse oximetry sensor 19 to an electrical connector 24. Electrical connector 24 is of any suitable construction for having a cooperatively shaped connector (not numbered) coupled thereto for wired transmission of data detected by pulse oximetry sensor 19 to a data processor 26 (shown schematically) so that the data can be analyzed and further utilized depending on the particular application. For example, in one example embodiment the data gathered by pulse oximetry sensor 19 is utilized by pressure generating device 4 to vary the treatment provided to patient P. Such variance may vary from minor "tweaks" or adjustments to the parameters of the treatment being provided to major changes such as changing from a therapeutic mode to a ventilator mode if the blood oxygen level of patient P drops below a predetermined value.

Figure 2B:
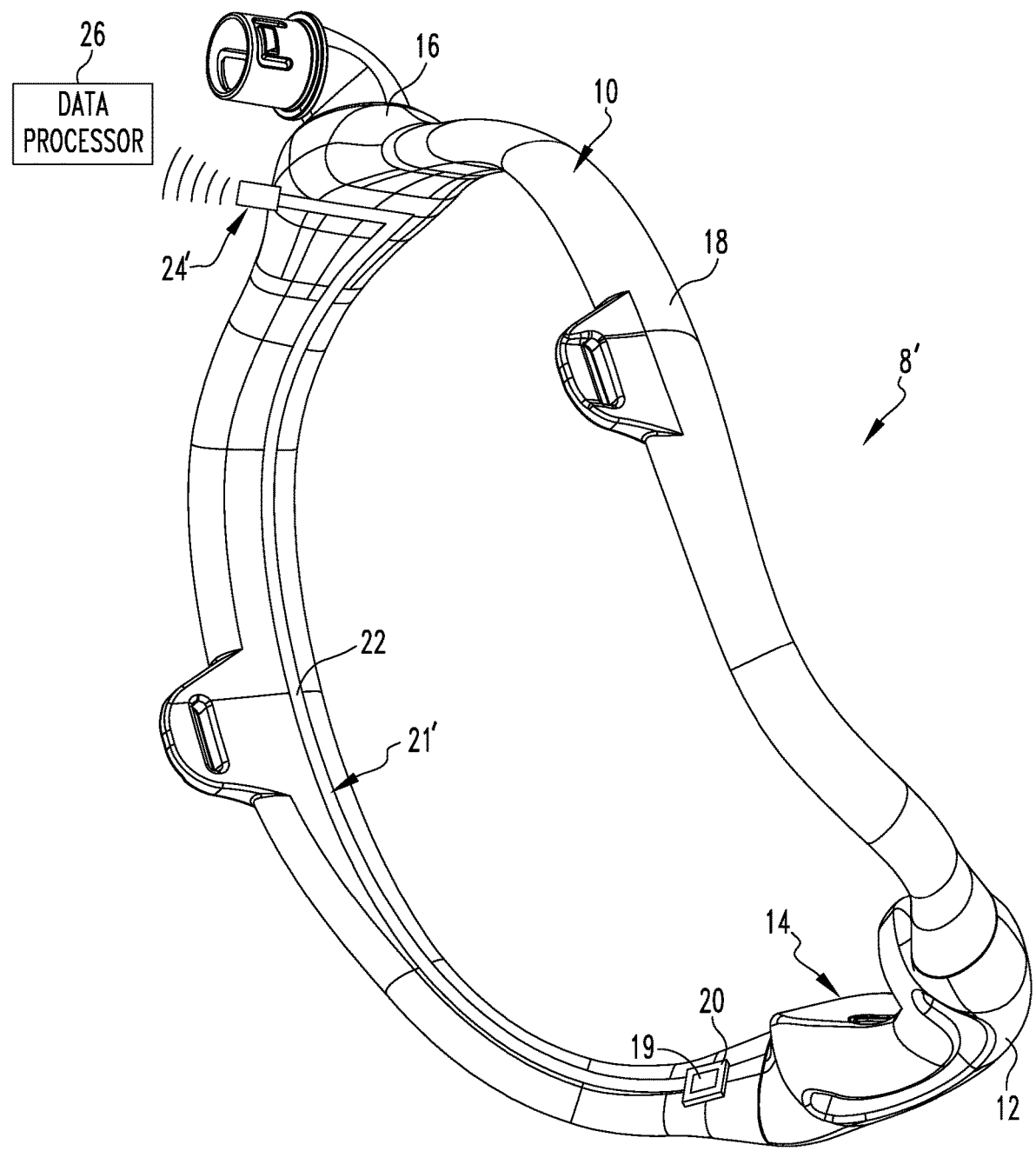
FIG. 2B is a partially schematic perspective view, similar to FIG. 2A, of another example embodiment of a mask for use in the system of FIG. 1 showing a patient contacting portion thereof.

FIG. 2B shows another example embodiment of the present invention similar to that shown in FIG. 2A except data communication arrangement 21' includes a wireless transmitter 24' that transmits data collected by pulse oximetry sensor 19 to data processor 26 via a wireless connection instead of a wired connection such as shown in FIG. 2A.

In one exemplary embodiment of the invention, flexible circuit 22 is positioned to lie adjacent to the face of patient P when tubing assembly 10 is disposed on the head of patient P. It is to be appreciated that flexible circuit 22 can be achieved in several ways, including but not limited to: spraying and adhering conductive material onto the surface of one of tubular portions 18, or printing a flexible circuit and affixing it to one of tubular portions 18 via adhesion, over-molding, or any other suitable arrangement.

In order to provide for more accurate readings and/or to provide for improved patient comfort, a skirt portion 28 may be provided adjacent to and around pulse oximetry sensor 19. Skirt portion 28 may be provided on (e.g., via any suitable coupling arrangement), or as an integral portion of, pocket 20 (such as shown in the examples illustrated in the figures) or as a separate member simply positioned around pulse oximetry sensor 19. Skirt portion 28 structured to shield pulse oximetry sensor 19 from ambient light when tubing assembly 10 is disposed on the head of patient P. In one exemplary embodiment of the invention, skirt portion 28 is composed from a flexible and opaque polymer. Perspective views of different skirt portions 28, 28', 28" formed as portions of pockets 20, 20' and 20" are shown in FIGS. 3A, 4A, and 5A. Sectional views of the different skirt portions 28, 28', and 28" shown in FIGS. 3A, 4A, and 5A are shown in FIGS. 3B, 4B, and 5B. FIGS. 3A and 3B show skirt portion 28 having a surface of uniform thickness with no protrusions disposed around pulse oximetry sensor 19, which is shown coupled to a printed circuit board (PCB) 29 (shown schematically) housed within pocket 20.

FIGS. 4A and 4B show skirt portion 28' formed as a number of petal-shaped protrusions 30 on one surface of pocket 20' around pulse oximetry sensor 19. The sectional view shown in FIG. 4B shows the number of petal-shaped protrusions 30 each extend from a first coupled end 30A disposed adjacent pulse oximetry sensor 19 to an opposite free end 30B disposed away from pulse oximetry sensor 19. Each protrusion 30 has an asymmetrically curved top edge 30C that peaks toward coupled end 30A and tapers downward toward free end 30B.

FIGS. 5A and 5B show skirt portion 28" which includes a thin base portion 32 extending upward from a surface of pocket 20" around pulse oximetry sensor 19, and a wider, bulbous portion 34 on thin base portion 32 opposite pocket 20" that also extends around pulse oximetry sensor 19.

It is to be appreciated that the skirt portions 28' and 28" shown in FIGS. 4A, 4B, 5A and 5B are included to provide additional cushioning to patient P when respiratory interface system 2 is disposed on the head of patient P as well as to generally avoid formation of marking on patient P at or about pulse oximetry sensor 19. It is also to be appreciated that skirt arrangements having alternate formations may be employed without varying from the scope of the present invention. It is also to be appreciated that skirt arrangements of different or varying durometers may be employed without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A tubing assembly for use in providing a flow of positive pressure breathing gas to a patient, the tubing assembly comprising:
    (a) a manifold portion structured to receive the flow of positive pressure breathing gas;
    (b) a first tubular portion and a second tubular portion, each tubular portion extending from the manifold portion to a distal end which is structured to be coupled to a patient interface for use in delivering the flow of positive pressure breathing gas to the patient;

(c) a reflectance pulse oximetry sensor positioned in or on one of the tubular portions,
wherein the sensor is structured to be disposed adjacent the patient when the tubing assembly is disposed on the head of the patient,
wherein each tubular portion is structured to be positioned on a respective side of the face of the patient forward of a corresponding ear of the patient when the tubing assembly is positioned on the head of the patient, and
wherein the sensor is positioned with respect to the one of the tubular portions such that when the tubing assembly is disposed on the head of the patient the sensor is positioned on a region of the patient's face extending between a forward boundary that extends between the patient's subnasale and labiale superius and a rearward boundary that extends between the patient's temple and helical root; and
(d) a data communication arrangement comprising:
(1) a flexible circuit positioned on the tubular portion on which the sensor is positioned, the flexible circuit extending between a first end electrically connected to the sensor and an opposite second end; and
(2) a data processor physically attached to the manifold and electrically connected to the second end of the flexible circuit, wherein the data processor controls the use of the sensor, including receiving signals from the sensor and converting the signals into a blood oxygen saturation value (SpO2) suitable for transmission away from the tubing assembly.

2. The tubing assembly of claim 1, wherein the sensor is adhered to a surface of the one of the number of tubular portions.

3. The tubing assembly of claim 1, wherein the sensor is coupled to the one of the number of tubular portions via over-molding.

4. The tubing assembly of claim 1, wherein a soft removable covering is coupled to the one of the number of tubular portions, and wherein the sensor is positioned in or on the removable covering.

5. The tubing assembly of claim 1, wherein the flexible circuit is structured to be disposed adjacent the patient when the tubing assembly is disposed on the head of the patient.

6. The tubing assembly of claim 1, wherein the one of the number of tubular portions comprises a skirt portion disposed about the sensor, and wherein the skirt portion is structured to shield the sensor from ambient light when the tubing assembly is disposed on the head of the patient.

7. The tubing assembly of claim 6, wherein the skirt portion comprises a flexible and opaque polymer.

8. The tubing assembly of claim 6, wherein the skirt portion includes a number of protrusions each of which, when viewed in a sectional view, has an asymmetrically curved top edge that peaks toward the center of the sectional view and tapers downward toward an edge of the sectional view, and wherein the number of protrusions provides additional cushioning when the tubing assembly is disposed on the head of the patient.

9. The tubing assembly of claim 6, wherein the skirt portion includes a number of protrusions each of which, when viewed in a sectional view, has a narrow stem portion arising from a surface of the skirt portion and a bulbous top edge, and wherein the number of protrusions provides additional cushioning when the tubing assembly is disposed on the head of the patient.

10. A mask for use in providing a flow of positive pressure breathing gas to a patient, the mask comprising:

(a) a tubing assembly structured to receive the flow of positive pressure breathing gas, the tubing assembly comprising:
(1) a manifold portion structured to receive the flow of positive pressure breathing gas; and
(2) a first tubular portion and a second tubular portion, each of the tubular portions extending from the manifold portion to a distal end;
(b) a patient interface coupled to the distal end of each tubular portion for conveying the flow of positive pressure breathing gas to an airway of the patient;
(c) a reflectance pulse oximetry sensor positioned in or on one of the tubular portions,
wherein the sensor is structured to be disposed adjacent the patient when the mask is disposed on the head of the patient,
wherein each tubular portion is structured to be positioned on a respective side of the face of the patient forward of a corresponding ear of the patient when the mask is positioned on the head of the patient, and
wherein the sensor is positioned with respect to the one of the tubular portions such that when the mask is disposed on the head of the patient the sensor is positioned on a region of the patient's face extending between a forward boundary that extends between the patient's subnasale and labiale superius and a rearward boundary that extends between the patient's temple and helical root; and
(d) a data communication arrangement comprising:
(1) a flexible circuit positioned on the tubular portion on which the sensor is positioned, the flexible circuit extending between a first end electrically connected to the sensor and an opposite second end; and
(2) a data processor physically attached to the manifold and electrically connected to the second end of the flexible circuit, wherein the data processor controls the use of the sensor, including receiving signals from the sensor and the signals generated into a blood oxygen saturation value (SpO2) suitable for transmission away from the tubing assembly.

11. The mask of claim 10, further comprising a data communication arrangement, the data communication arrangement comprising:
a flexible circuit positioned in or on the same one of the number of tubular portions in or on which the sensor is positioned, the flexible circuit extending between a first end electrically connected to the sensor and an opposite second end; and
one of either:
an electrical connector electrically connected to the second end, the electrical connector being structured to be electrically connected to a data processor, or
a wireless transmitter electrically connected to the second end, the wireless transmitter being structured to communicate wirelessly with the data processor.

12. A method for measuring a blood oxygen saturation level of a patient, the method comprising:
(a) providing the patient with a mask for use in providing a flow of positive pressure breathing gas to the patient, the mask comprising:
(1) a tubing assembly structured to receive the flow of positive pressure breathing gas, the tubing assembly comprising:
(i) a manifold portion structured to receive the flow of positive pressure breathing gas; and (ii) a first tubular portion and a second tubular portion, each tubular portion extending from the manifold portion to a distal end;

(2) a patient interface coupled to the distal end of each tubular portion for conveying the flow of positive pressure breathing gas to an airway of the patient;

(3) a reflectance pulse oximetry sensor positioned in or on one of the tubular portions, wherein the sensor is structured to be disposed adjacent the patient when the mask is disposed on the head of the patient, wherein each tubular portion is structured to be positioned on a respective side of the face of the patient forward of a corresponding ear of the patient when the mask is positioned on the head of the patient, and wherein the sensor is positioned with respect to the one of the tubular portions such that when the mask is disposed on the head of the patient the sensor is positioned on a region of the patient's face extending between a forward boundary that extends between the patient's subnasale and labiale superius and a rearward boundary that extends between the patient's temple and helical root; and (4) a data communication arrangement, the data communication arrangement comprising:

(1) a flexible circuit positioned or on the tubular portion on which the sensor is positioned, the flexible circuit extending between a first end electrically connected to the sensor and an opposite second end; and (2) a data processor physically attached to the manifold and electrically connected to the second end of the flexible circuit, wherein the data processor controls the use of the sensor, including receiving signals from the sensor and converting the signals into a blood oxygen saturation value (Sp02) suitable for transmission away from the mask; and (b) detecting the blood oxygen saturation level of the patient after the mask has been disposed on the head of the patient.

13. The method of claim 12, further comprising:

providing the flow of breathing gas to the patient via the mask; and altering the flow of breathing gas provided to the patient in response to the blood oxygen saturation level detected with the sensor.

* * * * *